(12) United States Patent
Hirsch

(10) Patent No.: US 9,163,906 B2
(45) Date of Patent: *Oct. 20, 2015

(54) ERGONOMIC GARMENT WITH CUT AND SHEARING RESISTANT STRAPPING AND AN ADJUSTABLE GIRTH AND LOCK

(71) Applicant: Yuval Hirsch, Herzeliya (IL)

(72) Inventor: Yuval Hirsch, Herzeliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/196,889

(22) Filed: Mar. 4, 2014

(65) Prior Publication Data

US 2014/0182038 A1    Jul. 3, 2014

Related U.S. Application Data

(63) Continuation of application No. 13/847,141, filed on Mar. 19, 2013, now Pat. No. 8,887,317.

(51) Int. Cl.
*A41D 13/05* (2006.01)
*F41H 1/02* (2006.01)
*A41B 9/12* (2006.01)
*A41D 1/06* (2006.01)

(52) U.S. Cl.
CPC ... *F41H 1/02* (2013.01); *A41B 9/12* (2013.01)

(58) Field of Classification Search
CPC ....... F41H 1/02; F41H 5/0464; F41H 5/0485; F41H 5/0492; F41H 5/0457; F41H 3/02; F41H 5/0407; F41H 5/0478; A41D 31/0061; A41D 31/0055; A41D 19/01511; A41D 13/0153; A41D 13/0587; A41D 13/0593; A41D 13/0525; A41D 13/0575; A41D 13/0581; A41D 19/01505; A41D 1/067; A41D 13/00; A41D 13/0002; A41D 13/015; A41D 13/0156; A41D 13/0506; A41D 13/0518; A41D 13/0537; A41D 13/0543; A41D 1/088; A41D 31/0044; A63B 71/1216; A63B 71/1225; A63B 71/12; A63B 2071/1233; A63B 71/08; A41B 11/02; A41B 1/08; A41B 9/04; A41B 9/12; A41B 9/02
See application file for complete search history.

(56) References Cited

U.S. PATENT DOCUMENTS

| 4,599,751 A | 7/1986 | Bouwhuis |
| 5,636,387 A | 6/1997 | Lundy |
| 8,887,317 B2 * | 11/2014 | Hirsch ............................ 2/406 |
| 2008/0206526 A1 | 8/2008 | Kim et al. |

FOREIGN PATENT DOCUMENTS

| CA | 2343707 A1 | 5/2000 |
| CA | 2343707 C | 5/2000 |
| CN | 2247429 Y | 2/1997 |
| DE | 4324398 A1 | 1/1995 |
| DE | 19948051 | 4/2001 |
| KR | 20090069670 | 7/2009 |

* cited by examiner

*Primary Examiner* — Bobby Muromoto, Jr.

(57) ABSTRACT

A protective garment of elastic ergonomic material with waist and thighs straps, and a central panel made of fabrics and obstacle elements in various patterns and combinations in order to delay, impede and deflect knife and scissors blades. Both waist and thigh structures enable adjustable girth via a lock and as such create a flexible and a non-elastic rigid and connected overall protective structure resistant to forcible attempts of undressing by pulling and or by cutting or shearing the garment.

20 Claims, 6 Drawing Sheets

FIG 4
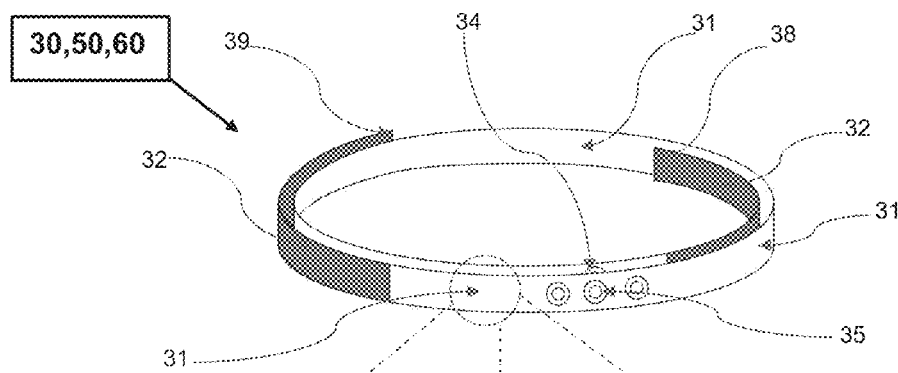
FIG 6
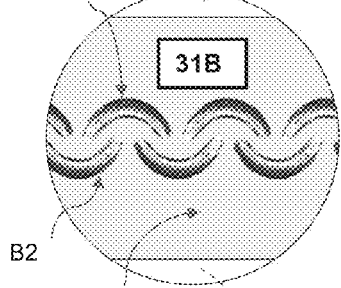
FIG 7
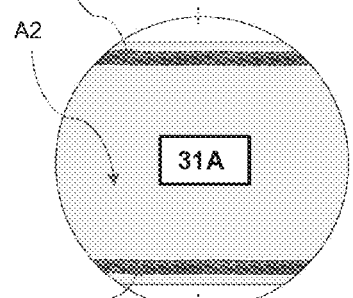
FIG 8
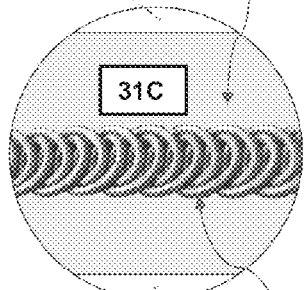
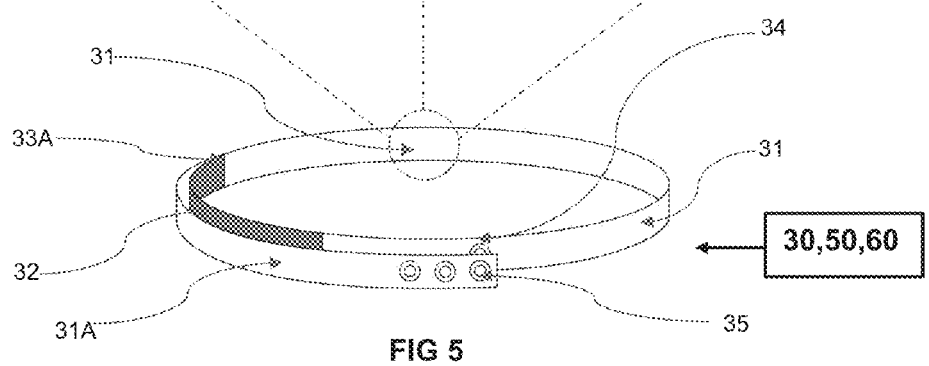
FIG 5

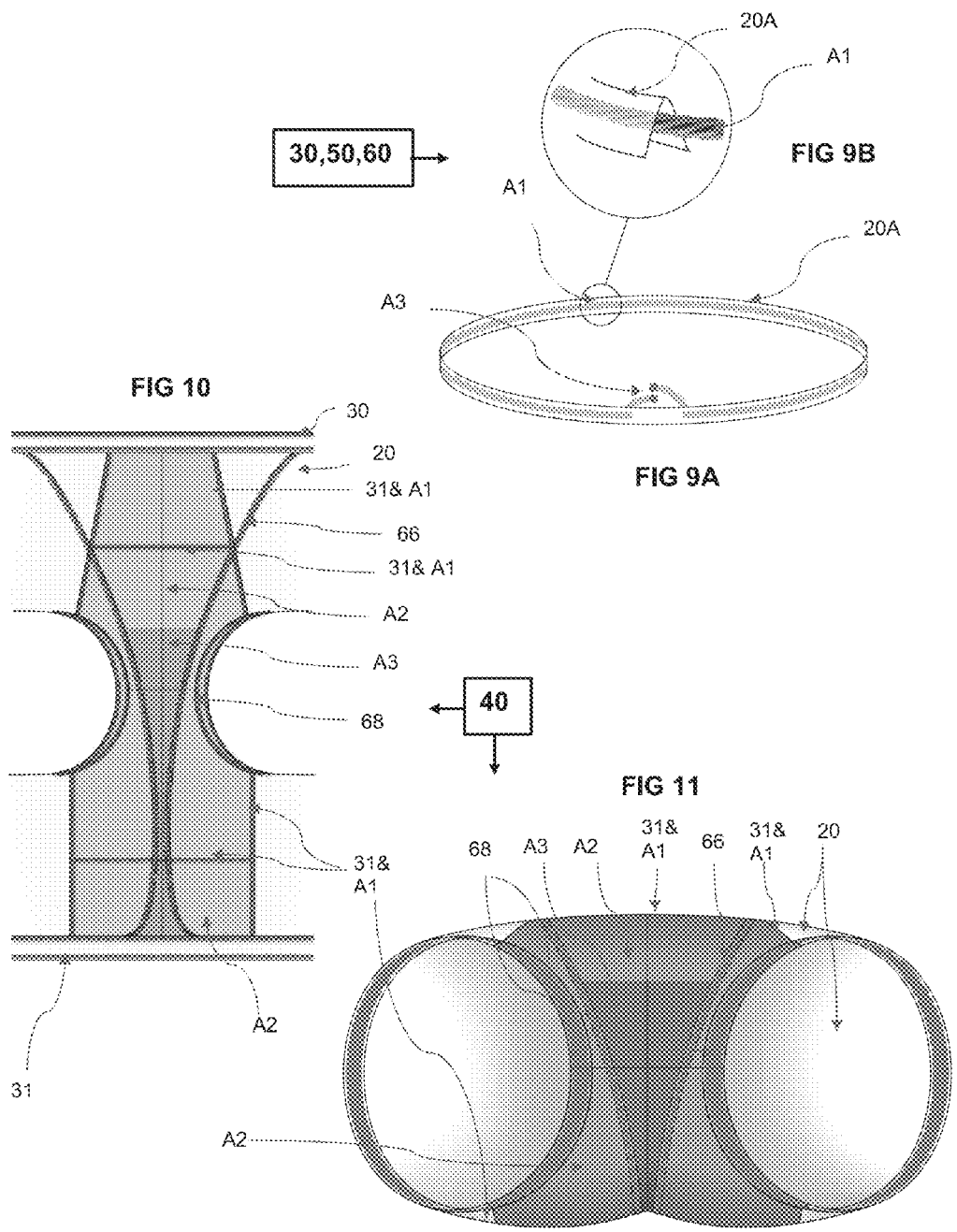

ERGONOMIC GARMENT WITH CUT AND SHEARING RESISTANT STRAPPING AND AN ADJUSTABLE GIRTH AND LOCK

CROSS-REFERENCE TO RELATED APPLICATION

This application is a continuation-in-part of and claims the benefit of the priority date of earlier filed U.S. Non-Provisional patent application Ser. No. 13/847,141 filed Mar. 19, 2013 for Yuval Hirsch, incorporated herein by reference in its entirety.

BACKGROUND OF THE INVENTION

Much can be said about the necessity to protect teenage girls and women from being sexual assaulted and raped. Indeed there are various products on the market that address this issue. However, it seems that none of the offered products are offering an effective passive resisting.

There are essentially two ways of providing protection against sexual assault: active and passive protection. Active protection includes physical resistant and various products which are all based on action from the victim; Self-defense skills can help to resist an attempted assault, but cannot be used in all situations and will not always be effective. Tools of self-defense are often not effective in all situations and depend on the courage and resourcefulness of the victim. Products such as pepper spray, tear gas, stun guns, weapons, etc. may allow the attacker to use the product against the victim.

Other products which offer passive protection are not dependent on the skill of the victim. However, such passive protection may cause serious injuries to the attacker such as the anti-rape female condom and an anti-rape tampon. Because some passive protection devices may be intrusive to the victim's comfort and privacy, such devices are not therefore very popular in the market either.

Another type of passive protection is the chastity belt and variations of add-on straps which are typically cumbersome and made of bulky and non-ergonomic materials and may be used as add-ons and therefore not used daily or replace garment and undergarment. What is needed in the market is a form-fitting and comfortable protective garment that may be worn every day and be easily laundered. There has therefore been a long felt need for an ergonomic and versatile protective garment that gives women a high degree of confidence and security for everyday use against assault and rape.

Invention is therefore an item of clothing that can be worn for daily activities that creates an effective barrier layer against physical sexual assault and can allow the wearer to passively resist an attacker.

However, such products can't be practically worn under clothing and are therefore not for daily use. What is needed in the market is a form-fitting and comfortable protective garment that may be worn every day and be easily laundered. There has therefore been a long felt need for an ergonomic and versatile protective garment that gives women a high degree of confidence and security for everyday use against assault and rape.

SUMMARY OF THE INVENTION

A protective garment of elastic ergonomic material covering a wearer from his or her waist to their thighs comprises waist and thighs straps, and central panel which (the mentioned straps and central panel) include cut resistant fabrics and comprise knife cut and scissors shearing obstacles in various patterns and combinations in order to delay, impede and deflect such tools' blades. Both the waist and thighs structure include adjustable girth via a lock and as such create a flexible and non-elastic rigid and connected overall protective structure resistant to forcible attempts of undressing by pulling and or by cutting or shearing certain areas of the garment.

Embodiments may include obstacles in a pattern of a flexible cable wire comprising twisted strands and wires in various structures made of steel or other alloy or with combination of soft filaments such as UHMWPE, providing cut and shear resistant; Additional obstacles embodiments may, alternatively or in combination of the above pattern, include spaced apart metal plates in not less of a dual row, so that each plate in the second row parallel to the space between the plates of the first row, providing that cutting by knife and scissors will be impeded or the very least be delayed due each row metal plates obstruction of the other row spacing. Although the metal plates are non-elastic, the spacing provides an overall flexible structure. Additional Obstacles embodiment may be designed as flat flexible structure string or wire and/or metal mesh or metal woven. All patterns may be integrated within the protective garment's mentioned strapping by weaving, braiding, knitting, adhesive, stitches, studs, and/or by coating (plastic, nylon or any other coating polymer material), by single type of integrated mode or by any combination of the mentioned modes.

The protective garment further comprises a waist strap, a crotch strap (or panel) and a strap for each thigh, all connected and disposed at an outer respective edge of the garment, each strap comprising mostly a non-elastic cut resistant fabric (such as UHMWPE and others) and the obstacle pattern permanently combined, integrated and disposed in configuration for delaying, impeding and deflecting a cutting attempting made by a pair of scissor and a knife at the mentioned straps.

The waist strap, the crotch strap and the strap for each thigh, are further designed to be adjustable to fit the wearer girth and physic to create non-elastic overall structure upon closing with a lock.

Girth adjustment embodiment may include a closed loop with partial elastic portion of the waist and each of the thighs straps connected an end of each non-elastic portion of the strap to another non-elastic portion of the strap to allow the wearer dressing-up. The elastic sub-portion is over-arched or is parallel by a non-elastic strapping portion which renders the entire strap non-elastic when joined via the lock.

Additional embodiment of the girth and physic adjustment may, alternatively or in combination of the above pattern, include non-elastic-non-closed loop at the waist and thighs strap area which create apertures of the non-elastic strapping structure before joining and locking thereof for allowing the wearer to dress up. Girth adjustment and closing the non-elastic strapping structure takes place upon joining or fastening of both sided of each of the strapping (narrowing the apertures) by a lock.

Additional embodiment of the girth and physic adjustment may, alternatively or in combination of the above patterns, include elastic-closed loop straps, of the waist and thighs area to allow the wearer to comfortably dress up. Current embodiment will include within (or outside) the waist and each thigh loop folding, a non-elastic cut resistant strap or wire made of the mentioned cut resistant yarns or the mentioned metal obstacle or combination thereof; the non-elastic protective skeletal structure takes place upon joining or fastening of both sided of each of the non-flexible cut resistant strapping by a lock.

Since a female's waist measurement is generally less than that of her pelvic area, the waist strap can be locked with non-elastic structure at a comfortable position and still prevent unwanted removal of the garment. The thigh to straps, after an initial adjustment by the wearer, prevent the leg openings from being lifted or shifted to the sides by someone else. The center panels are connected to both the waist and thigh straps to create a unified protective skeletal structure.

Other aspects and advantages of embodiments of the disclosure will become apparent from the following detailed description, taken in conjunction with the accompanying drawings, illustrated by way of example of the principles of the disclosure.

BRIEF DESCRIPTION OF THE DRAWINGS

FIG. 4 is a depiction of the waist and thigh straps of the embodiment of FIGS. 1 and 2, comprising non elastic loop with 2 elastic portions, connected to the garment at the inner and outer side of the straps folding, and points of joining the non-elastic overlapping portions, and a lock, in accordance with an embodiment of the present disclosure. This depiction does not show any specific pattern of the obstacle integrated within the strapping.

FIG. 5 is a depiction of additional embodiment of the waist and thigh to straps of the embodiment of FIGS. 1 and 2, comprising elastic portion and a non-elastic portion overarching the elastic portion, and points of joining the non-elastic portion of the loop and the non-elastic overarching portion, and a lock, in accordance with an embodiment of the present disclosure. This depiction does not show any specific pattern of the obstacle integrated within the strapping.

FIG. 6 is a close-up view of the obstacle in a pattern of spaced apart metal plates in a dual row incorporated into the strapping in accordance with one of the embodiment of the present disclosure.

FIG. 7 is a close-up view of the obstacle in a pattern of cable wire integrated into the strapping in accordance with one of the embodiment of the present disclosure.

FIG. 8 is a close-up view of the obstacle in a pattern of flat flexible structure string or waved wire integrated into the strapping in accordance with one of the embodiment of the present disclosure.

FIG. 9A is a depiction of additional embodiment of the waist and thigh straps of the embodiment of FIGS. 1 and 2 comprising all elastic-closed loop of the waist and thighs area and comprising in the waist and each thigh loop area a non elastic protective strapping or an obstacle in its regular form and a lock, in accordance with an embodiment of the present disclosure.

FIG. 9B is a close-up view of cable wire obstacle which is threaded within the lining of the strapping of embodiment depicted in FIG. 9A in accordance with one of the embodiment of the present disclosure.

FIG. 10 is an elevational depiction of a crotch strap; comprising obstacles in the pattern of the cable wire in accordance with an embodiment of the present disclosure.

FIG. 11 is a bottom perspective depiction of the protective garment showing the front-to-rear location of the crotch strap in accordance with an embodiment of the present disclosure.

Figure 1:
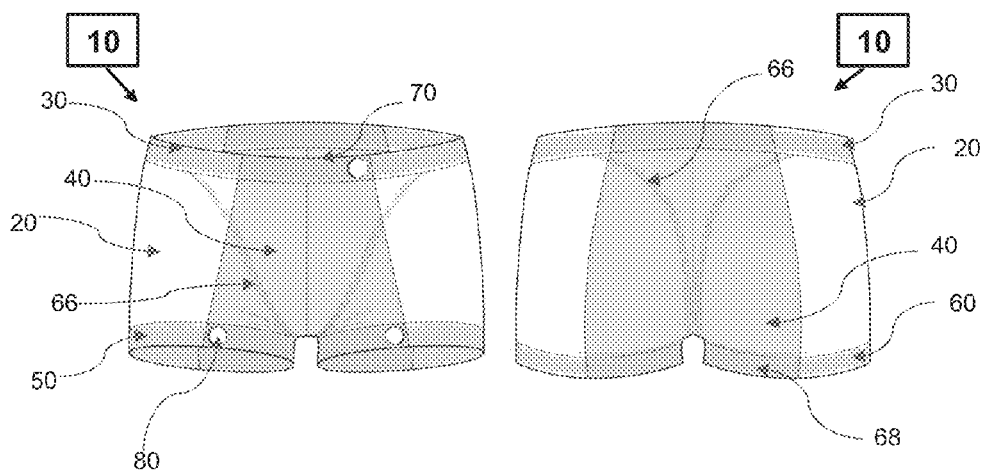
FIG. 1 is a front and rear perspective depiction of one embodiment of the protective garment (low waist line and short leg line) which may comprise a closed loop with only partial elastic portion of the waist and each of the thighs straps connected to the crotch panel (front-to-rear) and the strap locks in accordance with an embodiment of the present disclosure.

Throughout the description, similar and same reference numbers may be used to identify similar and same elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the claims.

Studies reviewing the statistics of resisting assault, whether by forceful or non-forceful means, show that resistance increases the chance of avoiding a completed rape without making the victim more likely to be physically injured. The disclosure therefore provides effective passive resistance that may benefit the wearer as studies predict. The disclosure is therefore an item of clothing that can be worn for daily activities that creates an effective barrier layer against physical sexual assault and can allow the wearer to passively resist an attacker, in addition to any other form of resistance they may be able to carry out at the time of an assault.

The disclosure offers a form-fitting and comfortable protective garment in a wide range of wearable items, including assorted types and styles of underwear, running shorts, traveling shorts, etc., suitable for different situations and the styles of individual users. The disclosed products are designed to be worn comfortably while still being able to frustrate an assault effectively. The disclosed garments are very difficult for someone else to remove by either force or stealth in situations where the victim cannot resist because she has had too much to drink, was drugged, or is asleep.

Furthermore, the disclosed articles of clothing are resistant to pulling, tearing and cutting while being comfortable to wear during normal activities and, as in the case of underwear, fit smoothly under form-fitting outer clothing.

The term 'obstacle' or "obstacle elements" as used throughout the present disclosure refers to various patterns and forms of steel or any other metal or other rigid core material, include the following: 1) wire rope comprising twisted strands and wires in various structures made of steel, stainless steel or other alloys, and can be structured of core, strand and filaments made of cut resistant yarns such as UHMWPE, glass fiber, Aramid fibers or in any combination thereof (including a rope combination of steel or any other alloy together with the mentioned soft synthetic yarns), providing cut and shear resistant. 2) spaced apart metal plates in not less of a dual row, so that each plate of the second row is positioned right above (or under) to the space between the plates of the first row, providing that cutting by knife and scissors will be impeded or the very least be delayed due each row metal plates obstruction of the other row spacing. 3) Flat flexible structured string, in various flexible shapes or wire; 4) Flexible structured of metal mesh which also refer to a metal chain or metal woven patterns. The wire rope, metal plates, string, wire, metal mesh, chain or woven, may be coated with nylon, plastic or other material, and are not limited by thickness although a favorable embodiment may comprise strapping with integrated obstacles of total thickness of no more than 3 millimeters.

The obstacle may be incorporated in a protective undergarment as a sole pattern or as a combination of couple or multiple patterns of the aforesaid and in various forms and any form of such obstacle (in one pattern or in combination) may be integrated within or attached to the strapping by weaving, braiding, knitting, adhesive, stitches, studs (which refer to any integration of obstacles to the strapping through penetration or embracing including staples and fasteners), and by coating (plastic, nylon or any other coating polymer material), by single type of integrated mode or by any combination of the mentioned modes; Obstacles may also be integrated to the protective garment not via strapping (application of the obstacle without strapping does not refer to the spaced apart metal plates)

Term 'deflecting' as used throughout the present disclosure refers to sliding or a slipping aside or a turning/twisting of a pair of scissor or knife blades from a straight course at an angle of incidence orthogonal to a garment strap comprising any of the mentioned obstacle pattern. The term 'jamming' refers to an obstacle lodging between the blades of a pair of scissors and impeding or preventing movement of the blades.

The term 'strap', 'strapping', panel and 'protective strap' or 'protective strapping' as used throughout the present disclosure are made of "regular" yarns (synthetic and natural) and may also comprise cut resistant fabrics such UHMWPE, glass fiber, Aramid fibers as well as other various cut resistant yarns, and comprising the obstacle which is integrated or attached by braiding (flat, tubular and piping), weaving, knitting, adhesive, stitches, studs (which refer to any integration of obstacles to the strapping through penetration or embracing including staples and fasteners) or by coating material such as nylon, plastic or any other polymer material, in any of the integration modes or in any combination thereof. The defined terms under this paragraph, also refers to an obstacle in its regular form (not integrated with fiber webbing in a strap).

The term 'garment' refer to any article of clothing worn against the body such as underwear and any article of clothing worn over clothing on the body such as outerwear including shorts, sports tights, traveling shorts, pants, etc. including an item comprising only the waist strap, both thigh straps and a crotch strap as described herein.

The term 'crotch strap' or 'crotch panel' refers to non-elastic (or limited elasticity) panel is the middle area from the waist line of the back side downwards to the crotch and up to the front waist line of the stomach side which comprise the obstacle elements. The middle section panel which includes the obstacle may be attached to the elastic and ergonomic material of the garment or may be the outer elevation of the garment with or without an elastic lining to underneath. The term 'crotch strap' may refer to a one piece panel or it may be fabricated from number of pieces of straps and various fabrics, in various widths and various obstacle patterns. The crotch panel may come in various embodiments and dimensions, may be fabricated in one or more pieces of fabric or straps, may comprise cut resistant fabric and/or regular fabric and the strapping and/or the obstacle elements integrated directly to the panel fabric; those multiply embodiments and variations share basic characteristics of: 1) non-elastic (or very limited elasticity) structure; 2) obstacle distribution to protect the loincloth and 3) strong hold of the waist and thighs straps for creating the protective skeleton structure.

The term 'waist strap' and 'thigh straps' refers to the strap loop which renders the waist and thighs and provide non-elastic protective strapping structure when the loop is joined with a lock in any of the various embodiments described herein and include, non-elastic protective strapping, partial non-elastic protective strapping, portion (or portions) of elastic strap (overarching or parallel by non-elastic protective strapping portion), complete elastic structure with inner or outer side non-elastic protective strapping (or obstacle non-integrated by strapping).

The terms 'skeleton structure' refer to the waist strap, the crotch strap and both thigh straps, which include the obstacle and which are integrated to create one close cut resistant non-elastic (or limited elasticity) structure allowing adjustable girth and closed with a lock. After joining with locks, in every embodiment, the center panels are connected to both the waist and thigh straps to create a unified protective core structure. The innovation of the protective skeleton structure is for keeping most of the garment regularly elastic (for example: in case of underwear) and ergonomic and by reinforcing only certain areas with a flexible and comfortable obstacle strapping structure, so that for any type of 'involuntary undressing', the assailant will be forced to overcome at least one of the skeleton's protective strapping for complete sexual offense. The skeleton structure is therefore designed to create an obstacle that will impede or the very least delay the offensive act, without downgrading the flexibility and ergonomics of the garment.

The term 'non-elastic' refers to a low degree of elasticity to completely non-elastic strap, strapping, join fabric structure to prevent unwanted removal of the garment, downwards the hips line and prevent the leg openings from being lifted or shifted to the sides.

The terms 'Lock' refers to a mechanical, electronic or magnet devise which holds parallel points of non-elastic waist strap to respective points for each of the non-elastic thigh straps, to create and hold a unified protective skeletal structure. A lock for the waist strap may be configured to open via a two-handed and relatively gentle operation; thigh strap locks are configured to be more difficult to open and may open only with a help of designed tool usually after underwear are safely removed. The thigh lock should not be opened for repeating use. Once the thigh loop strap is adjusted to a comfortable position and locked, the cone shape of the thigh will prevent the underwear from being lifted up to reveal intimate body area but may not prevent the underwear from being pulled down. Therefore the wearer may take off the underwear without opening the thigh lock.

An embodiment is disclosed comprising a practical garment, in particular an undergarment, which can be efficiently used as impediment against sex assault. The garment combines two features opposing in their nature. One feature may include a soft, ergonomic, flexible and elastic (at least in substantial parts) material and another feature may include strength, durability and resistant to a forcible attempt of pulling and to knife cut and a scissors shearing.

Prior art may not include one or both of the aforementioned features; those which are based only on a cut resistant fabric for covering the entire structure of the undergarment, such as Kevlar, do not provide a required degree of ergonomic elasticity for comfortable and sustained wear. Also, a suitable thickness of such fabric, as required for an undergarment, does not provide sufficient resistance to shearing in circumstances of excessive force and violence when professional grade scissors are used. Therefore, such art which includes features for delaying undressing by pulling will have very limited results as the undergarment can be removed by common scissors. Unlike prior art, the disclosure comprises mainly ergonomic-elastic fabrics while only certain areas in the waist, thigh and wide crotch straps comprise mainly non-elastic cut resistant fabrics and cut resistant obstacles (waist and thigh straps include a small part or parts which is/are elastic in order to ensure that straps are properly ergonomic fitting the wearer and an overlapping/parallel non elastic strap for eliminating the elasticity once the straps are fitted and adjusted).

Other prior art, based on metal meshes are unlikely to match the level of comfort, ergonomic fit, flexibility or level of thickness that the disclosure provides for protective, efficient and fitting daily use. Others which are based on belts (waist and vertical) made of leather or iron are not ergonomic, with excessive thickness. Furthermore belts have a structural weakness point due to its narrow coverage of the crotch which allow undressing by pulling (shifting aside) of the vertical belt resulting in no protection.

Other possible relevant art relates to cut resistant fabrics not designed for soft and ergonomic undergarments let alone preventing scissors shearing of the same. In addition, prior art based on the fabric itself (such as Aramid or UHMWPE) are based on multiple layers of same pattern elements and plates to prevent punctures and knife cuts on a broad area. However, the present disclosure includes a method of an obstacle which provides considerably greater protection at narrow coverage areas mostly in the outer side (edge) of the undergarment straps and in some portion of the middle section.

Embodiments of the present disclosure include scissors shearing and knife obstacle embedded in a strapping of an ergonomic garment creating an optimum obstacle and impediment to scissors shearing and a knife cutting. The combination of soft cut resistant material with flexible structure of steel or other rigid alloy providing a delay for most cutting tools for those which are design for cutting steel (such as steel cutter), the soft cut resistant yarn such as UHMWPE will reduce their cutting performance while the scissors will handle the soft yarn but will be impeded by the steel obstacles elements. Although the mentioned combination providing resistant to cutting and shearing it's thin and flexible structure allows having it embedded within certain areas of an ergonomic and comfort various types of garment and undergarments as disclosed herein.

The obstacle elements are concentrated only in certain areas of the undergarment on a minimum spreading area in order to provide an ergonomic undergarment which is protective from an aggressive attempt of undressing against the wearer's wish. Due to the small coverage area of the protective strapping the obstacle elements on the strapping may be varied in design to create real shearing and cutting obstruction that could not be achieved if such patterns were embedded in broader areas of the undergarments without having such undergarment becoming bulky and less ergonomic. The combined obstacle strapping of the disclosure is structured in a way that any type of undressing to enable forced intercourse requires require overcoming at least one protective strapping.

The present disclosure does not focus on creating a fabric per se which is cut-injury resistant nor cut resistant belt or strap, but provides features to prevent a considerable cut off of the undergarment via an impediment structure, incorporated particularly in the waist strap, thighs straps and crotch strap. The straps may all be interconnected in an embodiment of the disclosure for ergonomic daily use of the undergarment. Also, the disclosure includes a structural impediment or obstacle for preventing an aggressive undressing attempt by pulling the undergarment of a wearer.

FIG. 1 is a front and rear perspective depiction of one embodiment of the protective garment (low waist line and short leg line) which may comprise a closed loop with only partial elastic portion of the waist and each of the thighs straps connected to the crotch panel (front-to-rear) and the strap locks in accordance with an embodiment of the present disclosure. The protective garment 10 comprises of elastic ergonomic material 20 which covers a wearer from his or her waist to their thighs. The protective garment also comprises a waist strap 30, a crotch strap 40 (depicted in gray) and a strap for each thigh 50 and 60 which are all covered with ergonomic material 20 and disposed at an outer respective edge of the garment 10. The crotch and thigh straps are connected at the inner leg area here depicted at point 68. A flexible steel wire cable 66 may be attached within folding to both sides of the garment from the waist area down to the inner side of the legs. The protective garment 10 further comprises a waist strap lock 70, a left thigh strap lock 80 and a right thigh strap lock (also 80). Locks and components thereof may be located at different locations at the strap and may be within the ergonomic material which covers the waist and the thigh strap.

Figure 2:
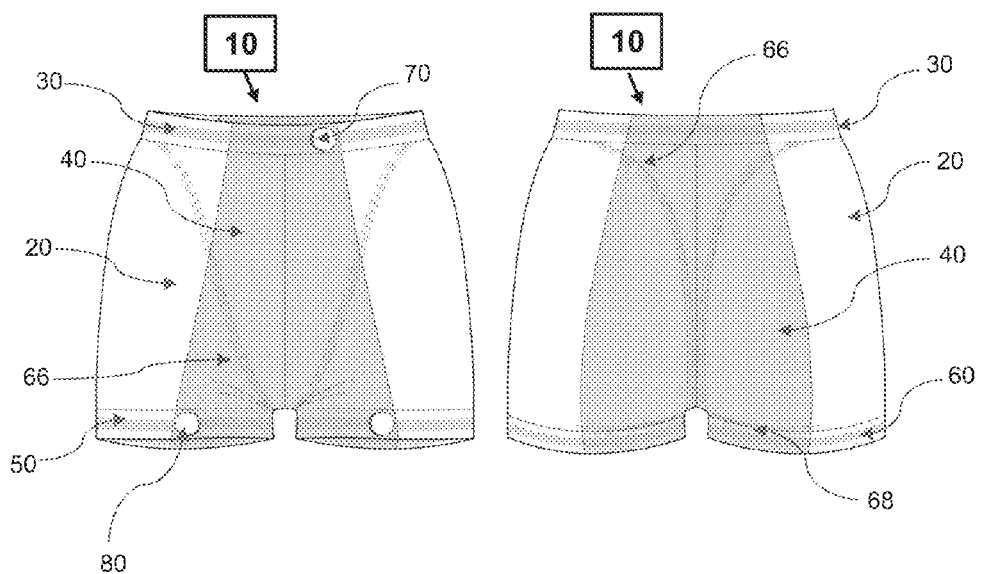
FIG. 2 is a front and rear perspective depiction of one embodiment of the protective garment (high waist line and long leg line) which may comprise a closed loop with only partial elastic portion of the waist and each of the thighs straps connected to the crotch panel (front-to-rear) and the strap locks in accordance with an embodiment of the present disclosure.

FIG. 2 is a front and rear perspective depiction of one embodiment of the protective garment (high waist line and long leg line) which may comprise a closed loop with only partial elastic portion of the waist and each of the thighs straps connected to the crotch panel (front-to-rear) and the strap locks in to accordance with an embodiment of the present disclosure. The protective garment 10 comprises of elastic ergonomic material 20 covers a wearer from his or her waist to their thighs. The protective garment also comprises a waist strap 30, a crotch strap 40 (depicted in gray) and a strap for each thigh 50 and 60 which are all covered with ergonomic material 20 and disposed at an outer respective edge of the garment 10. The crotch and thigh strap are connected at the inner leg area here depicted at point 68. A flexible steel wire cable 66 may be attached within folding to both sides of the garment from the waist area down to the inner side of the legs. The protective garment 10 further comprises a waist strap lock 70, a left thigh strap lock 80 and a right thigh strap lock (also 80). Locks and components thereof may be located at different locations at the strap and may be within the ergonomic material which covers the waist and the thigh strap.

Figure 3:
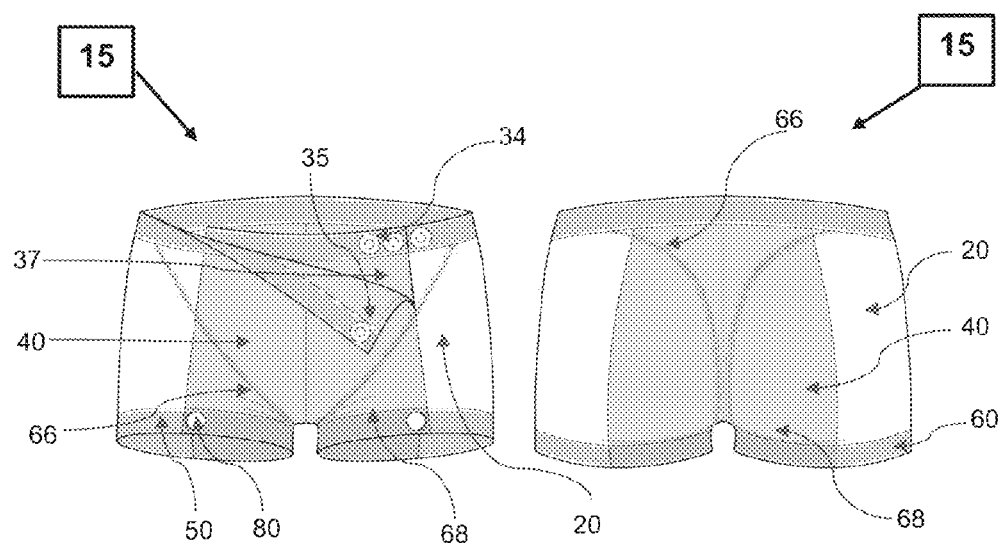
FIG. 3 is a front perspective depiction of different embodiment of the protective garment which may comprise non-elastic-non-closed loop at the waist and thighs strap area, the apertures thereof, connected to the crotch panel (front-to-rear) before joining with the locks.

FIG. 3 is a front and rear perspective depiction of additional embodiment of the protective garment which may comprise non-elastic-non-closed loop at the waist and thighs strap area, in a unfastened front view and rear view; The strapping at the waist and thighs areas are connected to the crotch panel (front-to-rear) but are not structured as a closed loops (creating apertures) before joining with the locks in accordance with an embodiment of the present disclosure. The protective garment 15 of elastic ergonomic material 20 covers a wearer from his or her waist to their thighs. The protective garment also comprises a waist strap which is non elastic non closed loop 45, an elastic lining for covering the apertures area 37 a crotch strap 40 (depicted in gray) and a strap for each thigh 50 and 60 (which are all covered with ergonomic material 20) disposed at an outer respective edge of the garment 15; The crotch and thigh straps are connected at the inner leg area here depicted at point 68, and a flexible metal wire cable 66 may be attached within folding to both sides of the garment from the waist area down to the inner side of the legs. The protective garment 15 further comprises (in this embodiment) a waist strap lock holes 34 and 35 which may alternatively be replaced with magnet or other lock mechanism not based on a passing through of the straps) waist strap lock (not depicted), and lock 80 for each.

FIG. 4 is a depiction of the waist and thigh straps of the embodiment garment 10 (FIGS. 1 and 2), comprising a non-elastic loop with 2 elastic portions in accordance with an embodiment of the present disclosure. The disclosed strap may comprise a non elastic portion loop with one or more elastic portions connected to the garment at the inner and outer side of the straps folding or lining thereof, and points of joining the non-elastic overlapping portions, and a lock (not depicted), in accordance with an embodiment of the present disclosure. In this embodiment, the waist strap 30 and each thigh strap 50 and 60 have the same loop strap structure comprising mainly non elastic strapping portion 31 which comprises the obstacle configured to have an adjustable girth via an elastic sub-portions 32 (on both sides) which are parallel to a non-elastic 31. In this embodiment the strap is attached to the folding/lining at both edges, on in the inner side of the elastic folding (not depicted) at point 38 and at the outer side of the elastic folding (not depicted) at point 39 and an adjustable respective lock 70 and 80 (not depicted) in order for the strap to only to stretch and not move and be repositionable within the lining; Otherwise the elastic portions may be attached to the parallel non elastic edges at adjacent points. The girth of each strap loop 30, 50 and 60 is adjustable via an elastic sub-portions 32 (on both sides) connecting an end of a respective strap to another portion of the strap. The elastic sub-portions 32 are overarched (on the outer side or the inner side) by non-elastic portions of the same strapping 31. This renders the entire respective strap 30, 50 and 60 when joined (spot 34/35) into a non-elastic loop when joined into a loop via the respective lock 70 or 80. A latching portion of both non-elastic strap parallel portions latch into the lock 70 (or 80) when inserted therein. Either the lock 70 placement is adjustable or the latching portions (34/35) are adjustable thereon in order that a wearer may adjust the girth of the waist strap loop for the best protective and best ergonomic fit. This depiction displays one lock-hole in the inner strap (34) and 3 lock-holes for girth adjustment in the outer strap (35), but additional adjustment lock-holes may be defined in the inner strap and the one lock-hole in the outer strap. All strap parts are located within the waist and thigh garment folding lining. After fitting the right loop size to the wearer waist or thigh, the lock is inserted from the garment inner side protective strapping and the other from the outer side of the garment through the latching portion (not depicted). A stretched strap loop may allow fitting to a larger waist and/or thigh and/or accommodate dressing and undressing according to a preference of a wearer of the disclosed protective garment. However, a strap loop that is too lose may allow the protective garment to be removed against the will of the wearer in compromising situations so caution should be taken to avoid overly liberal adjustments.

FIG. 5 is a depiction of a waist and thigh strap of garment 10 (FIGS. 1 and 2), comprising non elastic portion and elastic portion and a non-elastic portion overarching the elastic portion in accordance with an embodiment of the present disclosure The depicted strap loop comprises a non-elastic portion and an elastic portion and a non-elastic portion overarching the elastic portion and points of joining the non-elastic portion of the loop and the non-elastic over-arched portion. In this embodiment, the waist strap 30 and each thigh strap 50 and 60 have the same loop strap structure comprising mainly a non-elastic strapping portion 31 which comprises a pattern of wire rope obstacles configured to have an adjustable girth via an elastic sub-portion 32 and an adjustable respective lock 70 and 80 (not depicted). The girth of each strap loop 30, 50 and 60 is adjustable via the elastic sub-portion 32 connecting an end of a respective strap to another portion of the strap 31. The elastic sub-portion 32 is overarched by a strapping portion 31A entirely knitted to the undergarment inner side at the waist area which also comprises the obstacle elements connected to the non-elastic portion of the strap on spot 33A. This renders the entire respective strap 30, 50 and 60 when joined (to 34 and 35) into a non-elastic loop via the respective lock 70 or 80. A latching portion of the non-elastic waist strap latches into the lock 70 when inserted therein. This depiction displays one lock-hole in the inner strap (34) and 3 lock-holes for girth adjustment in the outer strap (35). Additional embodiments may comprise the 3 adjustment lock-holes in the inner strap and the one lock-hole in the outer strap. Either the lock 70 placement is adjustable or the latching portion is adjustable thereon in order that a wearer may adjust the girth of the waist strap loop for the best protective and best ergonomic fit. All strap parts are located within garment lining of the waist and thighs.

After fitting the right loop size to the wearer's waist or thigh, the lock is made by inserting one part from the garment inner side and the other from the outer side of the garment through the latching portion (not depicted). A stretched strap loop may allow fitting to a larger waist and/or thigh and/or accommodate dressing and undressing according to a preference of a wearer of the disclosed protective garment. However, a strap loop that is too lose may allow the protective garment to be removed against the will of the wearer in compromising situations so caution should be taken to avoid overly liberal adjustments.

FIG. 6 is a close-up view of obstacles in a pattern of spaced apart of metal plates in a dual row incorporated to the strapping in accordance with one of the embodiment of the present disclosure. The present depiction illustrate strapping comprising cut resisting fabric A2 and obstacles in a pattern of spaced apart metal plates in a dual row incorporated into the strapping in accordance with one of the embodiments of the present disclosure. Each plate of the second row B2 is positioned right above (or under) to the space between the plates of the first row B1 providing that cutting by knife and scissors will be impeded or the very least be delayed based on the metal plates row obstruction of the other row spacing; This pattern produces deflection and jamming of scissor blades as the rigid plates (distributed on soft strapping) are twisted due to the force applied with the shearing attempt; the spacing or intervals between the plates are also allows the strapping containing such pattern of obstacle will remain flexible.

FIG. 7 is a close-up view of cable wire integrated into the strapping in accordance with an embodiment of the present disclosure. The present figure depicts a close-up view of the inner side of the strapping 31 comprising a wire rope obstacle comprising twisted strands and wires in 7×19 rope structure, integrated to the strapping in accordance with one of the embodiment of the present disclosure. In this disclosure the strap include cut resistant fabric A2 and flexible structure of the steel cable/rope which include high number of filaments in a small diameter allows it to be incorporated within the strapping in various patterns; this depicted show a 2 wire rope in a straight loop A1 in both strap edges but can be based on only one straight cable or sinusoidal wave shape or any combination thereof. The flexible structure and thin diameter of the cable or rope provides a skeleton structure that will remain flexible and ergonomic as well as knife cut and scissors shearing resistant in the strapping area. The soft yet strong cut resistant yarn with the rigid yet very flexible wire cable will produce knife cut resistant and may also cause deflection and jamming to a blade off scissors; Any assailant will be forced to overcome at least one strapping for undressing the victim for sexual offense but such obstacle will impede or the very least delay the offensive act.

FIG. 8 is a close-up view of a flat flexible wire string structure integrated into the strapping in accordance with one of the embodiment of the present disclosure. Cut resistant fabric A2 and an obstacle pattern of flat flexible structure string or weaved shape wire may be integrated to the strapping. This depiction show closed rounded flat sting shape structure C1. The flexible structure and thin diameter of the string or wire provides that the skeleton structure based on such patterns will remain flexible and ergonomic while providing knife cut and scissors shearing obstacle that may imped or the very least be delayed.

FIG. 9A is a depiction of the waist and thigh straps of the embodiment garment 10 (FIGS. 1 and 2), comprising all elastic-closed loop of the waist and thighs area and comprising in the waist and each thigh loop folding (or attached to the strapping outer-side of the folding from the inside or outer-side of the garment) a protective strapping or an obstacle in its regular form without further integration with the strapping, creates a non-elastic protective loop by fastening the folded or otherwise connected strapping (or obstacle without strapping) by a lock, in accordance with an embodiment of the present disclosure. In this embodiment, the waist and each thigh have the same loop strap structure comprising elastic folding 20A and flexible non elastic obstacle A1 which comprises in this embodiment the pattern of wire rope obstacle configured to have an adjustable girth via fastening the non-elastic strapping A3 with a lock (not depicted).

FIG. 9B is a close-up view of cable wire obstacle which is threaded within the lining of the strapping of embodiment depicted in FIG. 9A in accordance with one of the embodiment of the present disclosure.

FIG. 10 is an elevational depiction of a crotch strap; the crotch panel may come in various embodiments and dimensions (widths and may be fabricated in one or more pieces of fabric or straps; The crotch panel may comprise cut resistant fabric and/or regular fabric and the strapping and/or the obstacle elements integrated directly into the panel fabric; The multiply embodiments and variations share the basic characteristics of: 1) non-elastic (or very limited elasticity) structure; 2) obstacle distribution to protect the loincloth and 3) strong hold of the waist and thighs straps for creating the protective skeleton structure. Current depiction of the crotch strap 40 comprises a non-elastic cut resistant fabric material A2 and the strapping includes obstacles in the pattern of wire cable at its edges 30,31&A1 Horizontal strappings in the upper and lower middle sections and may also comprise thin wire cable in the middle section (not depicted); Embodiment of the disclosure comprise double layers of cut resistant fabric A3. The crotch strap 40 is configured to permanently attach to the undergarment from a front and rear area and to a front portion of the waist strap 30 and to attach to a portion of the rear side of waist strap 31. The crotch strap 40 is configured to permanently attach at points 68 to a portion of each thigh non elastic portion of the strapping 50 and 60 in a crotch area where the thigh loops are closest each other. Besides the attachment to the waist and thighs straps, the crotch strap 40 is entirely attached to an inner side of the garment ergonomic fabric 20. The crotch area is also strengthened with additional flexible steel or fabric wire cable or any type of strap 66 attached in folding to the garment from the waist or the middle area down to the inner side of the legs. The crotch strap 40 may further comprise ventilation notches and/or perforation holes for undergarment breathing. A pad (not depicted) may be configured to attach to the crotch strap in a front portion of the undergarment, the pad comprising cushioning and absorbent materials.

FIG. 11 is a bottom perspective depiction of the protective garment showing the front-to-rear location of the crotch strap; In accordance with an embodiment of the present disclosure. The present depiction illustrates the front-to-rear location of the crotch strap and does not show any specific obstacle pattern of the protective garment. Throughout the present depiction, similar and same reference numbers may be used to identify similar and same elements depicted in other figures of multiple embodiments. The undergarment elastic ergonomic fabric 20 (in fair grey) is viewed both in an outer side of the fabric and viewed through the thighs loops (sleeve). Thigh strapping 50, 60 is viewed in medium grey although the straps may be located within the sleeve of ergonomic elastic fabric and be connected to the crotch strap at 68. Also the location of the crotch strap may be located in the undergarment as depicting the strapping connection of the crotch straps with the thigh straps and the location of further protection obstacles to the crotch area A2, A3, 68 and 31&A1.

Figure 12A:
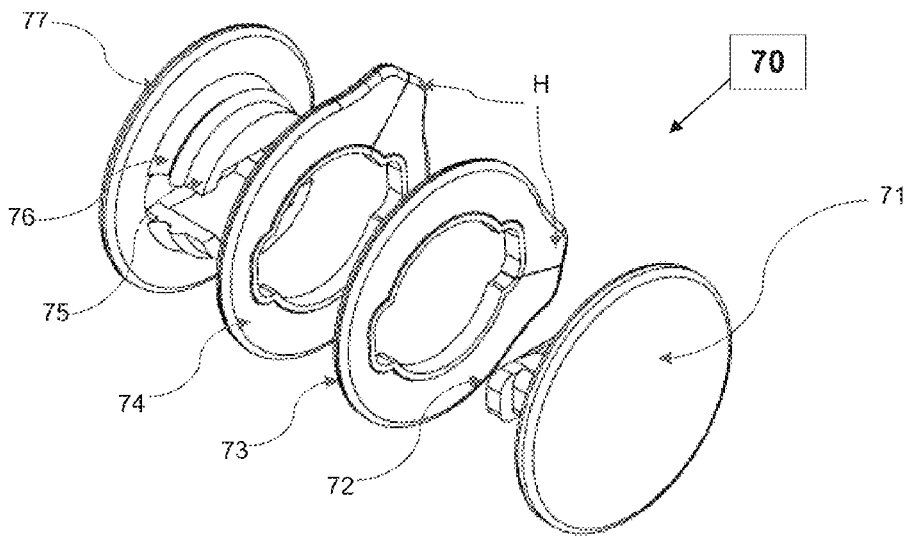
FIG. 12A is an exploded perspective depiction of a waist strapping lock showing component parts in accordance with an embodiment of the present disclosure.

FIG. 12A is an exploded perspective depiction of the waist strapping lock 70 showing component parts in accordance with an embodiment of the present disclosure. Throughout the present depiction, similar and same reference numbers may be used to identify similar and same elements depicted in other figures of multiple embodiments. Part 71 is designed to be either located in the undergarment lining or in the outer side, and can be permanently fixed to the non-elastic strapping portion 31 which is connected to the undergarment lining from the inner side. For esthetic reasons it could be placed outside the undergarment lining, holding both the undergarment waist lining and strapping or also as a detached component that will inserted by the wearer. The lock has a rectangular prominent tooth 72 which is designed to fit at a certain angle to the opening of parts 73, 74 and 77. Parts 73 and 74 are braced to part 77 and are able to rotate (clock wise) on niches 75 and 76 respectively, and are designed (parts 73 and 74) to rotation via the cams or small handles H will be at a different and offset "clock wise" point when openings of parts 73 and 74 are matching to part 72. The locking mechanism works by adjusting the parts so the opening of 73 and 74 are matching part 72 which is passing through all strapping (not depicted) and parts 73 and 74 and finally through the rear part 71. In this position, the undergarment wearer rotates parts 73 and or 74 and now opening niche in part 73 or 74 will no longer be in line or offset with respect to the rectangular prominent tooth 72. Therefore it is hooked in part 77 for which it held by 73 and 74. Since there are two rotating discs (73, 74) each is planned for (at least) 12 stops as similar to clock pointers (hours and minutes), the random rotation of the two discs allows 132 combinations to open the lock. The lock components may be made of steel and resist also a very strong pulling by an attacker. Multiple amounts of locks may be produced for each of the 132 combination and may be randomly assembled to the undergarment. The wearer should remember the combination of parts 73 and 74 specific rotation for adjusting the lock for opening, in a simple fashion of remembering the "hour and minute".

In an embodiment of the disclosure, the waist strap lock comprises two rotatable disks (73 and 74) and a central hub (71) configured to pass through all strapping and the disks (73 and 74) and the straps and lock everything together.

The hub comprises at least one tooth and each disk comprises a complementary notch therein configured to allow the at least one tooth to pass there through and lock when the disks are offset rotated in relation thereof.

Figure 12B:
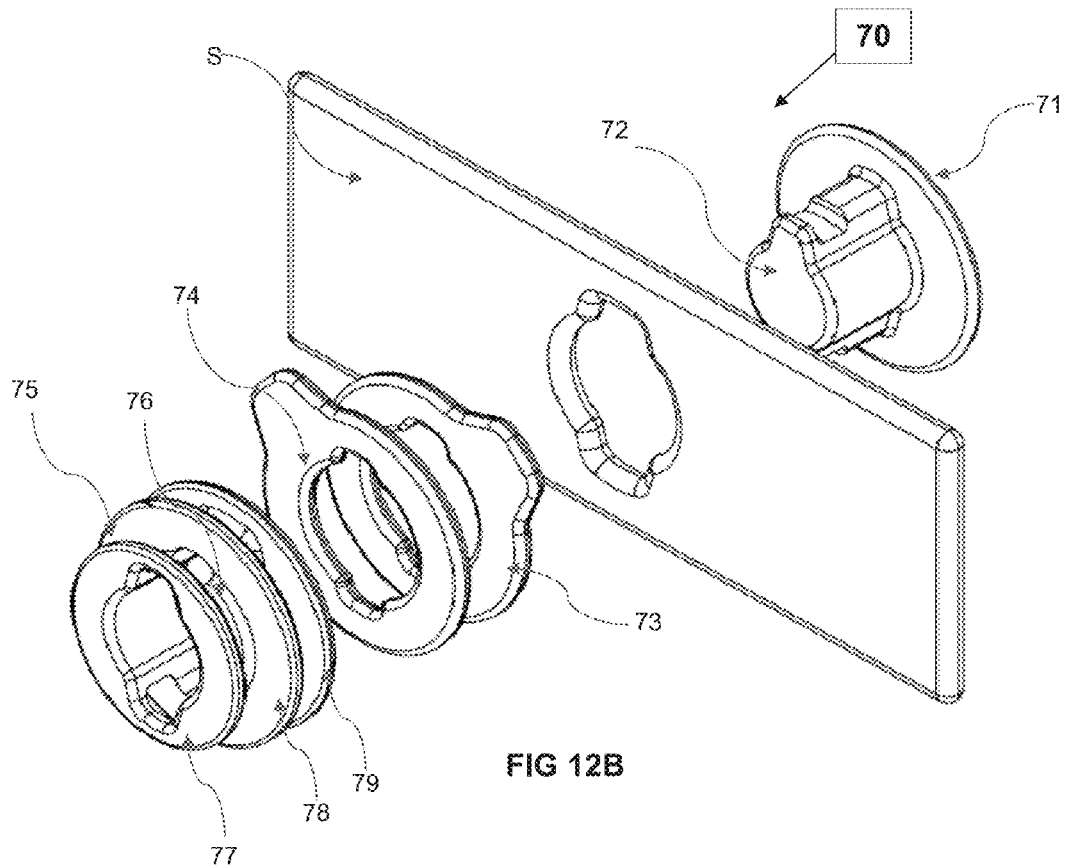
FIG. 12B is additional angle of an exploded perspective depiction of a waist strapping lock showing component parts in accordance with an embodiment of the present disclosure.

FIG. 12B is additional exploded perspective depiction of the waist strapping lock 70 showing component parts with placing relation to a strapping with in accordance with an embodiment of the present disclosure. The rear part 71 will not be fully attached to the strapping. Parts 73,74,76,75 are all permanently fixed to the strapping; The strap is held in-between parts 78 and 79; rotates parts 73 and 74 are braced to part 77 and are able to rotate (clock wise) on niches 75 and 76.

Figure 12C:
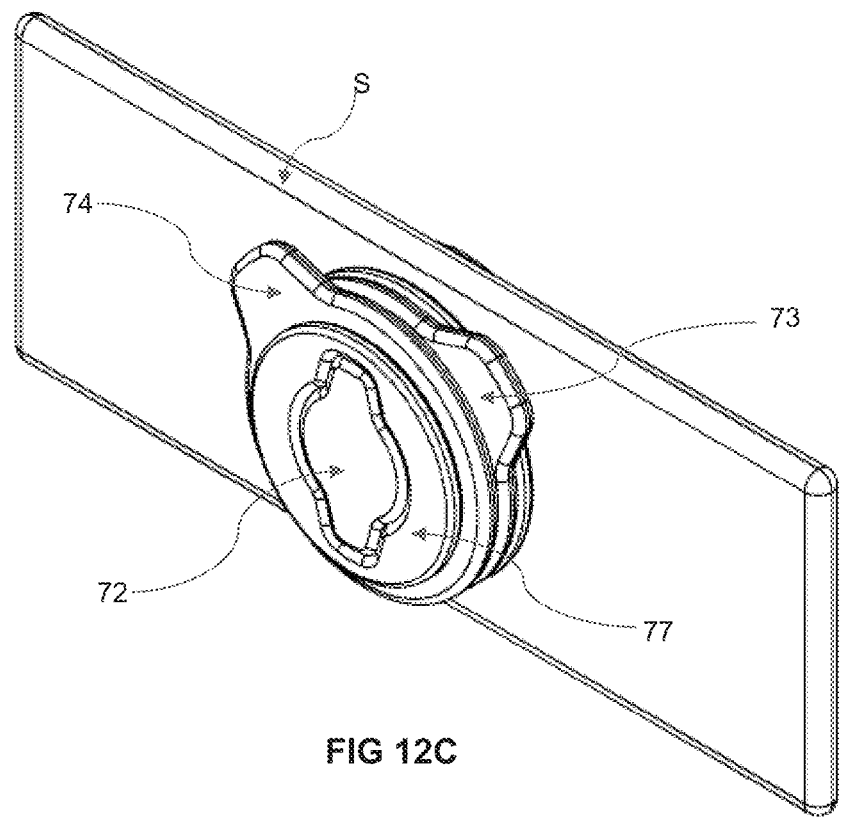
FIG. 12C is a closed perspective depiction of a waist strapping lock showing component parts in accordance with an embodiment of the present disclosure.

FIG. 12C is a closed perspective depiction of the waist strapping lock 70 showing component parts when the lock is fastened; in this disclosure rectangular prominent tooth 72 is fully inserted via parts 73,74 and 77 (78 and 79 are not depicted).

Figure 13:
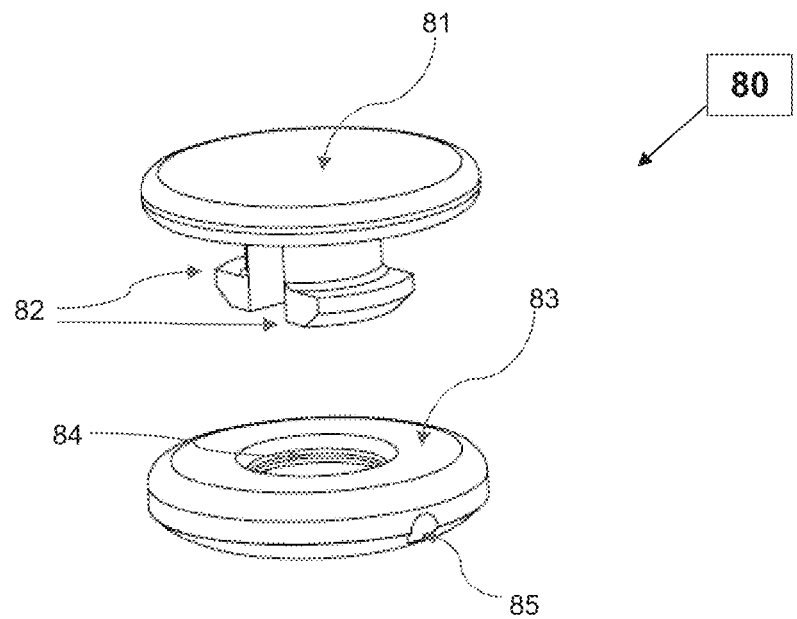
FIG. 13 is a partially assembled perspective depiction of a thigh strapping lock showing component parts in accordance with an embodiment of the present disclosure.

FIG. 13 is a partially assembled perspective depiction of a thigh strapping lock showing component parts in accordance with an embodiment of the present disclosure. Throughout the present depiction, similar and same reference numbers may be used to identify similar and same elements depicted in other figures of multiple embodiments. The waist lock 70 is designed for repeating opening, since the girth of the waist must be adjusted for each dressing and undressing. However, a lock 80 for each thigh strap is not configured for repeated use. Once the thigh loop strap is adjusted to a comfortable position and locked, the cone shape of the thigh will prevent from the underwear to be lifted up and reveal intimate body areas but will not prevent pulling down and therefore the wearer could take off the underwear without opening the thigh lock. The front part 81 is designed to be either located in the undergarment lining or in the outer side, and can be permanently fixed to the non-elastic strapping portion 31 which is connected to the undergarment lining from the inner side. But for esthetic reasons it could be placed outside the undergarment lining, holding both the undergarment waist lining and strapping or can be also not connected permanently to the undergarment and inserted by the wearer when using. The mechanism of lock 80 rounded head 81 is big enough not to slip off in case of pulling. The bottom side comprises two teeth 82 that are designed to slightly approach each other while they are pushed into the opening 84 of lock 80 rear part 83 and when pushed and inserted to rear part 83, at its middle there are niche which teeth 82 are released from the squeeze and placed in that niche. Since the teeth 82 are released in the middle part of 83 there is no direct hold of 82 for squeezing by hand. The opening 84 is narrower than the girth of teeth like parts 82 lower end, therefore part 81 could not be reopened unless both teeth 82 are squeezed and pulled out. Since it is anticipated that reopening of lock 81 might be needed for various reasons, lock include tiny hole 85 of both sides of part 83 (only one side is depicted) which allow pushing each of teeth 82 using a hard wire tool with both hands at the same time. This mechanism ensures that opening will be done only under certain condition more likely under the wearer cooperation.

Embodiments of the present disclosure may further comprise a trigger wire disposed in the straps, the trigger wire configured to trigger an alarm circuit in the event an open circuit occurs anywhere in the wire. Embodiments may further comprise an ampoule disposed adjacent a front of the undergarment, the ampoule configured to broadly and forcefully disperse a bright stain and/or a bright paint and/or a deterring smell onto the undergarment and onto an attacker who cuts a trigger wire or destroys a strap lock.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Notwithstanding specific embodiments of the invention have been described and illustrated, the invention is not to be limited to the specific forms or arrangements of parts so described and illustrated. The scope of the invention is to be defined by the claims and their equivalents to be included by reference in a non-provisional utility application.

What is claimed is:

1. A protective garment of elastic ergonomic material covering a wearer from his or her waist to their thighs, comprising:
    a flexible and cut impedance strapping comprising at least one obstacle shaped in a cut-resistant and cut deflecting pattern; and
    a waist strap, a crotch strap and a strap for each thigh, each strap interconnected to another strap via the garment, each cut resistant obstacle thereon permanently attached to the garment and each strap configured to have an adjustable girth via an elastic subportion configured to render the respective strap non-elastic based on a lock.

2. The protective garment of claim 1, wherein the strapping comprises cut resistant fabric and metal elements configured to provide resistance to a knife cut and to shearing via a pair of scissor blades.

3. The protective garment of claim 1, wherein the obstacles are patterned as a wire rope of twisted strands and wires of steel and other alloys configured in a flexible structure and pattern including connected spaced apart metal elements in at least one row and plurality of spaced apart metal plates in at least a dual row thereof, and a flat flexible metal string, metal mesh, metal chain and a metal woven pattern and cut resistant yarns or any combination thereof.

4. The protective garment of claim 1, wherein the obstacles are integral to at least one of the strapping and the garment by a braid, a knit, a weave, a stitch, a stud wherein a stud may also refer to staples and fasteners, and by coating with plastic, nylon, silicon and any other polymer material.

5. The protective garment of claim 1, wherein the waist strap and each thigh strap are configured to have an adjustable girth via the lock and comprise a non-elastic portion including the cut obstacle(s) permanently disposed thereon and an elastic portion that may be connected to an end of each portion of the strap to another non-elastic portion of the strap, or only to one end portion of the strap, the elastic portion over-arched by a non-elastic strapping portion including the cut obstacle element(s) which render the entire strap non elastic based on the non-elastic portions joined thereto.

6. The protective garment of claim 5, wherein one or more elastic portion(s) are connected to the garment at an inner side of the strap folding on one edge and at the outer side of the strap folding on the other edge, which renders the entire strap non elastic when joined the non-elastic overlapping portions via the lock.

7. The protective garment of claim 6, wherein the elastic portions may be connected on both ends thereof to an overlapping and non-elastic parallel portion of the strap.

8. The protective garment of claim 1, wherein the waist strap and each thigh strap further comprise all elastic closed-loop straps configured to allow adjustable girth and create a non-elastic skeleton structure based on respective locks.

9. The protective garment of claim 1, wherein the waist strap and each thigh strap further comprise non-elastic and non-closed loop apertures configured to allow wearing and undressing via adjustments per the wearer's girth and joined via the lock.

10. The protective garment of claim 1, wherein the crotch strap comprises a non-elastic and cut resistant material and the cut obstacles permanently disposed thereon are permanently attached to a front portion of the waist strap and to a rear portion of the waist strap and to both thigh straps along an inner side of the garment where the thigh loops are closest each other.

11. The protective garment of claim 1, wherein the crotch strap further comprises at least one of a plurality of ventilation notches and perforation holes for undergarment breathing and a pad configured to attach to the crotch strap in a front portion of the garment, the pad comprising cushioning materials.

12. The protective garment of claim 1, further comprising at least one flexible cable which may refer to a strap attached to a front and a rear of the garment from the waist or middle area down to an inner side of the legs, the cables configured to provide additional resistant against an attempt to shift and pull-up aside a leg opening in the bottom crotch area.

13. The protective garment of claim 1, further comprising a trigger wire disposed in the straps, the trigger wire configured to trigger an alarm circuit in the event an open circuit occurs anywhere in the wire.

14. The protective garment of claim 1, further comprising an ampoule disposed adjacent a front of the undergarment, the ampoule configured to broadly and forcefully disperse at least one of a bright colorant and a deterring smell onto an attacker who one of cuts a trigger wire and destroys a strap lock.

15. The protective garment of claim 1, wherein a lock for the waist strap opens via a two-handed operation.

16. The protective garment of claim 1, wherein the waist strap lock comprises at least one rotatable disk and a central hub configured to pass through both a non-elastic parallel portion of the strapping and an overarched portion and lock the straps together, the hub comprising at least one tooth and each disk comprising a complementary notch therein configured to allow the at least one tooth to pass there through and lock when the disks are offset rotated in relation thereof.

17. The protective garment of claim 1, wherein a lock for each thigh strap opens via a designed tool after the garment is removed from the wearer.

18. The protective garment of claim 1, wherein a covering fabric adjacent an area of the lock defines an opening configured to allow access to the lock.

19. A protective garment comprising a front and rear center panel connected to both a waist and a thigh strap loop comprising a partially elastic and flexible strapping with at least one cut resistant obstacle and an adjustable girth skeleton structure closeable via a lock, the adjustable girth skeleton structure configured to create a unified protective non-elastic skeleton portion based on joining via the lock of the garment allowing at least one fully ergonomic portion.

20. The protective garment of claim 19, wherein an involuntary undressing of the garment requires cutting, tearing, shearing at least one of the skeleton structure portions of the garment.

* * * * *